(12) United States Patent
Kuo et al.

(10) Patent No.: US 11,864,969 B2
(45) Date of Patent: Jan. 9, 2024

(54) PRIORITIZATION OF THREE DIMENSIONAL DENTAL ELEMENTS

(71) Applicant: Align Technology, Inc., San Jose, CA (US)

(72) Inventors: Eric E. Kuo, San Jose, CA (US); Igor Kvasov, Dolgoprudny (RU); Anna Egorova, Moscow (RU); Sergey Gagarin, Moscow (RU)

(73) Assignee: Align Technology, Inc., San Jose, CA (US)

( * ) Notice: Subject to any disclaimer, the term of this patent is extended or adjusted under 35 U.S.C. 154(b) by 190 days.

(21) Appl. No.: 17/346,051

(22) Filed: Jun. 11, 2021

(65) Prior Publication Data

US 2021/0298875 A1    Sep. 30, 2021

Related U.S. Application Data

(63) Continuation of application No. 15/824,621, filed on Nov. 28, 2017, now Pat. No. 11,033,360, which is a continuation of application No. 14/716,537, filed on May 19, 2015, now abandoned, which is a continuation of application No. 13/410,196, filed on Mar. 1, 2012, now Pat. No. 9,037,439.

(60) Provisional application No. 61/486,138, filed on May 13, 2011.

(51) Int. Cl.
*G16H 50/50* (2018.01)
*A61C 9/00* (2006.01)
*G06F 30/00* (2020.01)
*A61C 7/00* (2006.01)
*A61B 1/00* (2006.01)
*A61B 1/24* (2006.01)

(52) U.S. Cl.
CPC .......... *A61C 7/002* (2013.01); *A61B 1/00022* (2013.01); *A61B 1/000095* (2022.02); *A61B 1/24* (2013.01); *A61C 9/004* (2013.01); *A61C 9/0053* (2013.01); *A61C 9/0073* (2013.01); *G06F 30/00* (2020.01); *G16H 50/50* (2018.01); *G06T 2210/62* (2013.01)

(58) Field of Classification Search
CPC ... A61B 1/000095; A61C 7/002; A61C 9/004; A61C 9/0053; A61C 9/0073; G06T 2210/62

See application file for complete search history.

(56) References Cited

U.S. PATENT DOCUMENTS

| 5,975,893 A | 11/1999 | Chishti et al. |
| 6,227,851 B1 | 5/2001 | Chishti et al. |
| 6,299,440 B1 | 10/2001 | Phan et al. |
| 6,318,994 B1 | 11/2001 | Chishti et al. |

(Continued)

*Primary Examiner* — Akash Saxena
(74) *Attorney, Agent, or Firm* — Shay Glenn LLP

(57) ABSTRACT

The present disclosure includes methods, systems, and devices for prioritization of three dimensional dental elements. One method for prioritizing three dimensional dental elements includes receiving a virtual initial dental data set (IDDS) of teeth having spatial information regarding the positions of a number of teeth in the virtual IDDS with respect to each other for presentation of the teeth in a virtual three dimensional space to be viewed on a user interface, setting prioritization values of a number of elements of one or more of the number of teeth, and prioritizing the number of elements to be selected by a user based upon their prioritization values.

20 Claims, 5 Drawing Sheets

(56) References Cited

U.S. PATENT DOCUMENTS

| | | |
|---|---|---|
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,063,532 B1 | 6/2006 | Jones et al. |
| 7,074,038 B1 | 7/2006 | Miller |
| 7,074,039 B2 | 7/2006 | Kopelman et al. |
| 7,108,508 B2 | 9/2006 | Hedge et al. |
| 7,134,874 B2 | 11/2006 | Chishti et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,108,189 B2 | 1/2012 | Chelnokov et al. |
| 8,126,726 B2 | 2/2012 | Matov et al. |
| 8,152,523 B2 * | 4/2012 | Sporbert ............ A61C 9/0046 433/24 |
| 8,260,591 B2 | 9/2012 | Kass et al. |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 8,949,730 B2 * | 2/2015 | Giasson ............ A61C 13/0004 715/764 |
| 9,037,439 B2 * | 5/2015 | Kuo ................ A61B 1/000095 703/7 |
| 9,060,829 B2 | 6/2015 | Sterental et al. |
| 9,125,709 B2 | 9/2015 | Matty |
| 9,179,988 B2 * | 11/2015 | Dumitrescu ............ A61C 5/77 |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197727 A1 * | 10/2004 | Sachdeva ................ A61C 7/00 433/24 |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2007/0099147 A1 * | 5/2007 | Sachdeva ............. A61C 9/0046 433/24 |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2011/0224955 A1 * | 9/2011 | Fisker ................ B33Y 50/00 703/1 |
| 2013/0204599 A1 | 8/2013 | Matov et al. |
| 2015/0254420 A1 * | 9/2015 | Kuo ................ A61C 7/002 703/11 |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |

* cited by examiner

PRIORITIZATION OF THREE DIMENSIONAL DENTAL ELEMENTS

CROSS REFERENCE TO RELATED APPLICATIONS

This application is a continuation of U.S. patent application Ser. No. 15/824,621, filed on Nov. 28, 2017, titled "PRIORITIZATION OF THREE DIMENSIONAL DENTAL ELEMENTS," now U.S. Pat. No. 11,033,360, which is a continuation of U.S. patent application Ser. No. 14/716,537, filed on May 19, 2015, titled "PRIORITIZATION OF THREE DIMENSIONAL DENTAL ELEMENTS," now abandoned, which is a continuation of U.S. patent application Ser. No. 13/410,196, filed on Mar. 1, 2012, titled "PRIORITIZATION OF THREE DIMENSIONAL DENTAL ELEMENTS," now U.S. Pat. No. 9,037,439, which claims the benefit of U.S. Provisional Application No. 61/486,138, filed on May 13, 2011, titled "PRIORITIZATION OF THREE DIMENSIONAL DENTAL ELEMENTS," each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

The ability to visualize and manipulate key digital dental references in a three dimensional (3D) scene can be important for efficiency, making 3D computerized graphics more efficient, at times, than physical manipulation of models. However, digital dental references may be incorrectly identified in these 3D computerized graphics as a result of certain surfaces (e.g., interproximal surfaces) being blocked out due to crowding. Furthermore, identifying a correct surface may be difficult when teeth are worn down, broken, or restored to an atypical shape.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
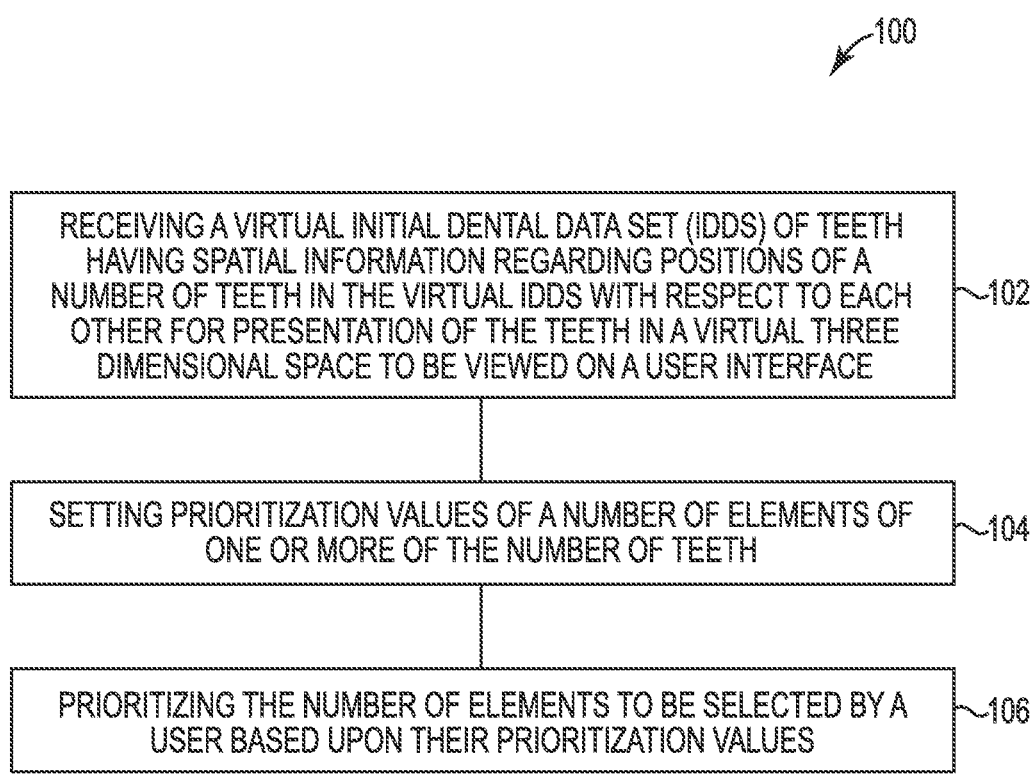
FIG. 1 illustrates a method for prioritizing three-dimensional (3D) dental elements according to one or more embodiments of the present disclosure

Embodiments of the present disclosure include methods, systems, and devices for prioritization of three dimensional (3D) dental elements. For example, one or more embodiments include a method of prioritizing 3D dental elements that includes receiving a virtual initial dental data set (IDDS) of teeth having spatial information regarding the positions of a number of teeth in the virtual IDDS with respect to each other for presentation of the teeth in a virtual 3D space to be viewed on a user interface, setting prioritization values of a number of elements of one or more of the number of teeth, and prioritizing the number of elements to be selected by a user based upon their prioritization values.

In the following detailed description of the present disclosure, reference is made to the accompanying drawings that form a part hereof, and in which is shown by way of illustration how a number of embodiments of the disclosure may be practiced. These embodiments are described in sufficient detail to enable those of ordinary skill in the art to practice a number of embodiments of this disclosure, and it is to be understood that other embodiments may be utilized and that process, electrical, or mechanical changes may be made without departing from the scope of the present disclosure.

Embodiments of the present disclosure can be utilized, for example, to solve the problem of landmarks being incorrectly identified as a result of certain surfaces, such as interproximal surfaces, being blocked out due to crowding. Embodiments also can solve the problem of trying to identify the correct surface when teeth are worn down, broken, or restored to an atypical shape, making the identification difficult to perform accurately. By using the context in which the tooth is positioned, the landmark can be properly labeled with one or more desired landmark labels despite the non-conventional position and/or shape of the tooth or tooth-related surface.

The process of labeling the digital landmarks therefore depends on the user's ability to visualize the surrounding dental-related geometries, as well as the relevant landmarks, and the ability to position the landmarks in the proper position in 3D space. This may entail the desire to see through objects and access a reference point behind the object, and/or for the object to be adhered to a certain surface contour.

A 3D object, when viewed, may have a natural spatial sequence of prioritization, meaning that the surface closest to the viewer has first priority, and the surface farthest away from the viewer has the least. It may be desirable for 3D manipulation purposes to orient the object in a certain view, but disrupt the natural sequence of prioritization. In other words, it may be desirable to be able to select the second closest surface first instead of the first closest object.

For example, in a number of embodiments, a user can specify which "layer" of an object (e.g., a tooth) should always take priority. By doing this, the user can create automation commands, for example, whereby keystrokes on the keyboard will advance to the next priority independent of the view.

Furthermore, in a number of embodiments, a user can choose to have relative priority, meaning that rather than having to specify which object (e.g., a tooth) has priority over the other, there may be general classifications, whereby a type of element has priority over another family of elements. For instance, in a number of embodiments, teeth surfaces may always have priority over gingival (gum) surfaces. In such embodiments, it may be that a user will always be able to select the teeth before the gums, but can advance to the gums by selecting a keystroke, for example.

In some embodiments, a priority as to which objects are to be rendered transparent and which to be left opaque can be given depending on which object is selected. This allows for user input or an automatic (determined via computing device executable instructions) determination as to which object is made more transparent and which object is more opaque (e.g., solid).

FIG. 1 illustrates a method 100 for prioritizing 3D dental elements according to one or more embodiments of the present disclosure. At 102, a virtual IDDS of teeth having spatial information regarding the positions of multiple teeth in the virtual IDDS with respect to each other for presentation of the teeth in a virtual three dimensional space to be viewed on a user interface is received.

An IDDS and/or virtual IDDS representing an initial tooth arrangement may be obtained in a variety of ways. For example, a patient's teeth may be imaged to obtain digital data using direct or indirect structured light, X-rays, three-dimensional X-rays, computer-aided tomographic images or data sets, magnetic resonance images, photographic reconstruction, and/or other imaging techniques.

Prioritization values of a number of elements of one or more of the number of teeth are set at 104. In some embodiments, prioritization values can be set by a user, such as a dental service provider, and in other embodiments, prioritization values can be determined by instructions executed by a processor. Prioritization values can also be set, for example, based on elements, landmarks, or dental objects in a virtual IDDS.

Elements can include, among others, a tooth and/or teeth in the virtual IDDS, a reference point on and/or around a tooth and/or teeth in the virtual IDDS, a dental object, and/or a dental landmark, such as, for example a crown, a root, a surface, a cusp, a cingulum, a ridge, a developmental groove, etc. Elements can also include, for instance, a combination of the previously discussed elements. In some embodiments, an element is attached to a tooth and/or teeth in the virtual IDDS.

At 106, elements to be selected by a user are prioritized based upon their prioritization values. In some embodiments, using the prioritization values, a first element in the number of elements can be allowed to be selected before a second element in the number of elements, where the first and second elements may have overlapping portions. The first and second elements may also be located on a same tooth or on different teeth. Based on the selection, in some embodiments, one of the first element and the second element can be rendered more (e.g., automatically rendered) transparent, while the other element is rendered more opaque.

Elements can also be manipulated along a tooth and/or teeth in a virtual IDDS, and this can influence decisions about an element's transparency. For instance, in some embodiments, such as for manipulating objects attached to a tooth where the relevant surface is facing the user, the tooth can be more opaque, but a neighboring tooth can be made more transparent.

In such embodiments, the tooth may not be made invisible because the adjacent tooth can be a beneficial reference in the positioning of the reference point on the more opaque tooth. A line of sight of a user can also be considered, and a particular element in the virtual IDDS can be automatically rendered more transparent based on the line of sight consideration. In some embodiments, digital dental landmarks can also be identified on a tooth and/or teeth in the virtual IDDS despite unconventional and/or inconvenient positions of the landmark.

The identified digital dental landmark can also be transferred to a different virtual dental data set in a number of embodiments. For example, a landmark may be adjusted on a first model (e.g., a virtual IDDS) to be propagated across different time points of the same model for a same patient. In such embodiments, the different virtual dental data set may include a virtual dental data set representing a different point in time than the virtual IDDS for a same patient. The different virtual dental data set may also include a virtual dental data set representing a different tooth configuration than that of the virtual IDDS for the same patient.

In such embodiments, the contexts of a particular view may result in easier landmark location identification as compared to a different view. For example, a reference point A selected from a particular perspective X of a configuration 1 may result in an increased ease in landmark location identification as compared to finding the same reference point A at the same perspective X at a different configuration 2.

FIGS. 2A-2F illustrate a number of example virtual IDDS and 3D dental elements of the virtual IDDS according to one or more embodiments of the present disclosure. With respect to FIG. 2A, during the manipulation of reference point 218 adhered to tooth 216 (e.g., tooth #10), tooth 214 (e.g., tooth #9) can be automatically made partially transparent or selected by a user to be made partially transparent because the visualization of the user-facing surface of tooth 216 can be beneficial as discussed above. Selecting reference point 218, for example, allows the user to move this reference point 218 along the surface of tooth 216, while using the outline of tooth 214 and its references (e.g., reference point 212 adjacent to reference point 218) to make decisions as to where to position the reference point 218, among other benefits.

In some embodiments, the user can switch to the manipulation of references (e.g., reference point 212) which are adhered to tooth 214, but this may not change the transparency of tooth 214, because even though the reference is positioned on 214, the user may desire to see through the tooth 214 in order to properly position it relative to teeth 214 and 216 (and tooth 216's references). In some such embodiments, reference point 212 can only be moved around the surface of tooth 214, such that the reference point can be moved around the tooth surface, but cannot be removed from the tooth surface.

Figure 2A:
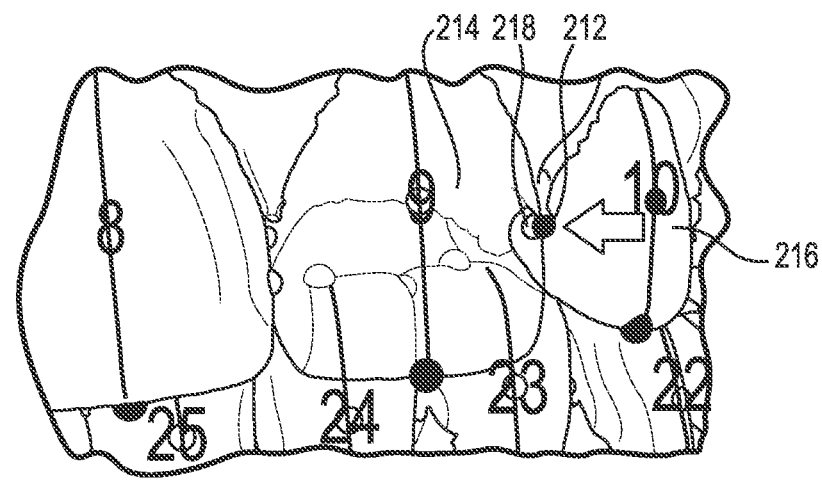
FIGS. 2A-2F illustrate example virtual initial dental data sets (IDDS) and 3D dental elements of virtual IDDS according to one or more embodiments of the present disclosure.
Figure 2B:
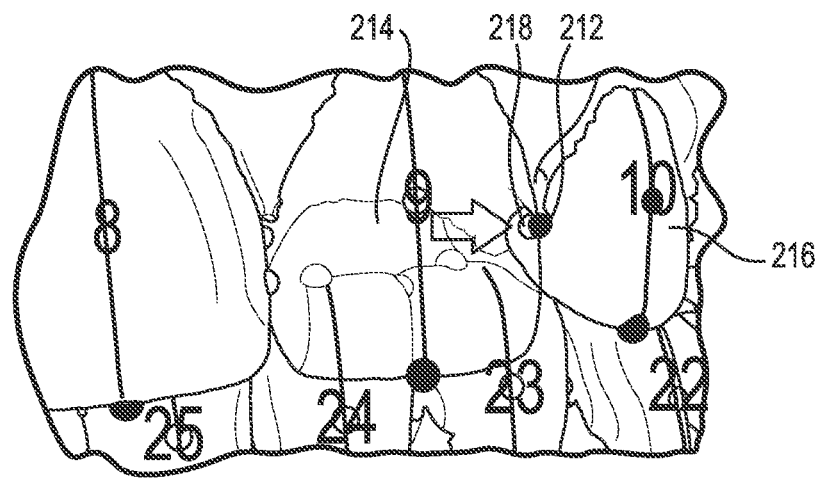

Therefore, depending on the orientation of the model relative to the user and the desired reference point to be selected, certain teeth and/or objects (e.g., gingiva, implants, references) in the scene can be made visually more transparent, as illustrated in FIG. 2B, so that the user can see behind the object, while preserving the ability to utilize the reference as a cue for orienting and/or positioning the reference(s). In the example illustrated in FIG. 2B, a first tooth 214 (e.g., tooth #9) is transparent, while a second tooth 216 (e.g., tooth #10) remains opaque.

Figure 2C:
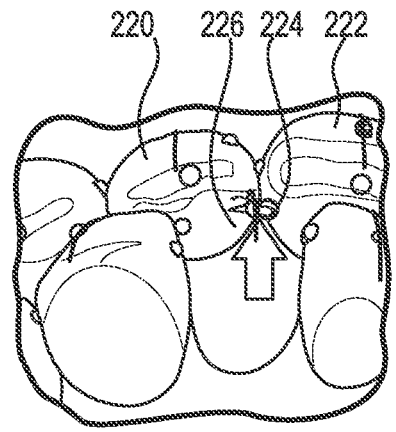

For example, as illustrated in FIG. 2C, a lower tooth 226 (e.g., tooth #26) may be hidden in order to adjust references pertaining to a view from underneath. For example, tooth 226 can be hidden (e.g., automatically hidden) to allow for adjustments of particular references. For example, the "incisal edge" reference 224 can be accessed and/or manipulated in light of upper teeth 220 and 222, without lower tooth 226's geometry getting in the way, which would be the case if it were not rendered in transparent mode.

Figure 2D:
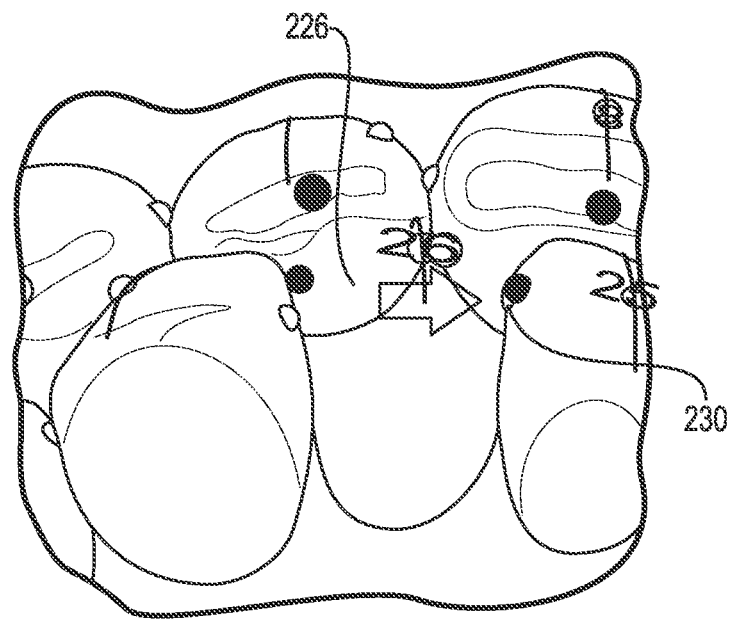

In an example, the incisal edge reference 224 on tooth 226 may not be seen or accessed because tooth 226 is in the way. As shown in FIG. 2D, however, an adjacent "interproximal" contact point 230 can also be manipulated as described previously for upper teeth 214 and 216 (e.g., teeth #9 and #10) with respect to FIG. 2A.

In such embodiments, computing device executable instructions can provide the ability to consider the line of sight of the user, (e.g., from the perspective of the user viewing via a user interface, such as a display) and the ability to render certain teeth more transparent allows the user to manipulate key dental references including points, lines, shapes, and the teeth themselves, without the hindrance of the object blocking the positioning of the desired reference. In such embodiments, the user can be able to effectively "see behind" the blocking object, while using the object's shape and/or position in the decision making process. Such embodiments may be useful when viewing the 3D space with a two dimensional or 3D user interface.

Furthermore, the user may be able to select the reference points and/or move them "through" the object in front of it. In other words, the blocking object can be ignored by the computing device executable instructions by giving the reference objects behind the object in front a higher priority in terms of selection.

In various embodiments, if a pointer is on a reference object, the reference object selection can be given a higher priority than the selection of the object which is visually (and in real life, physically) in front of the reference in the virtual space. In some such embodiments, this can allow the reference to be selected even though there may be another object in front of it.

Figure 2E:
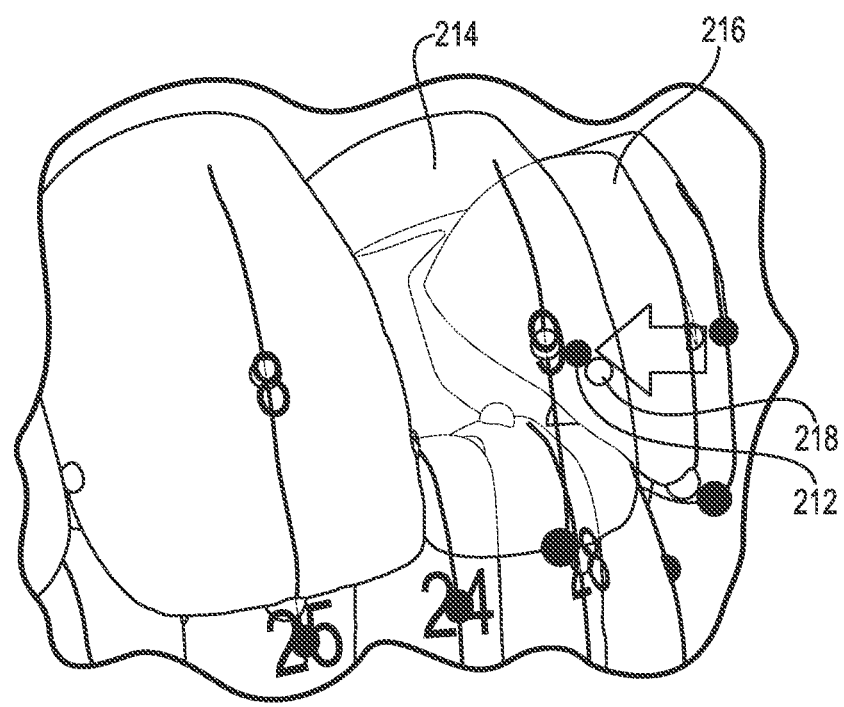

An example of the concept of prioritization is discussed with respect to FIG. 2E. For instance, tooth 214 (e.g., tooth #9), which is spatially "in front" of contact points 212 and 218, has one contact point that belongs to tooth 214 (e.g., tooth #9) and another to the adjacent tooth 216 (e.g., tooth #10).

From this view, both contact points 212 and 218 are sitting behind tooth 214. This view however, is the desired viewpoint because teeth naturally have an area where the contact points should be located. The problem is that tooth 214 is in the way of manipulation of the contact points.

In some embodiments, a "visual" prioritization could be to select the tooth 214 first when selecting an object in the area of the contact points 212 and 218 because tooth 214 is in front. However, by giving the contact point references a higher prioritization, tooth 214 is not selected when the user selects the pixels containing both tooth 214 and a contact point reference. Rather, the contact point references can be given a higher priority and therefore can be selected instead of the tooth. In some embodiments, this can result in an ability to adjust and/or view the contact point references even though tooth 214 is in front of the contact points 212 and 218.

Figure 2F:
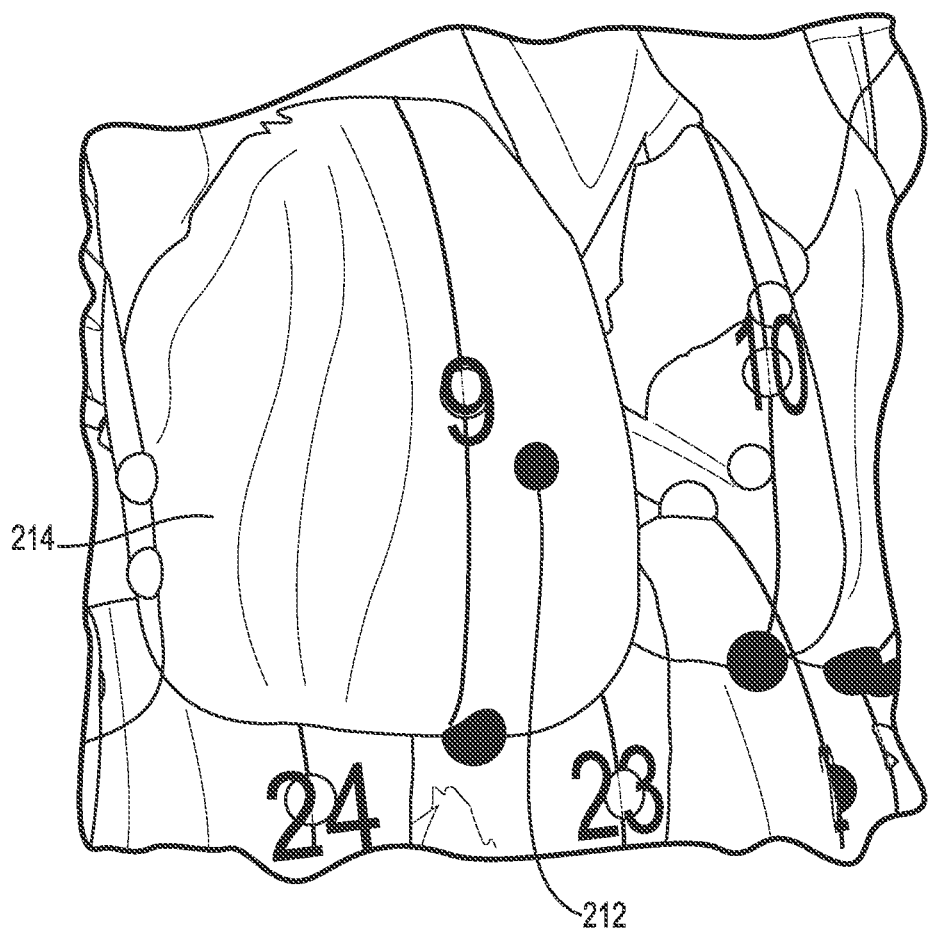

Another aspect of prioritization, in some embodiments, can be the positioning and/or placement of objects which are spatially behind other objects. In trying to move point 212, as illustrated in FIG. 2E, the typical behavior is for point 212 to be released after being selected on the front surface of tooth 214 (e.g., tooth #9) because this is the surface which is spatially in front, and normal selection behavior releases the object on the front-most object in spatial priority. The behavior taught in the present disclosure, however, is for point 212 to slide along the "back" or distal surface of tooth 214 and not brought to the front as shown in FIG. 2F.

In some typical concepts, the contact point behind the tooth is released on the front surface of the tooth. However, in the present disclosure, a contact point can be positioned on the "back" interproximal surface of the tooth even though the front surface is closer to the user in the user's view. In other words, the typical visual-spatial relationship (e.g., closest object to the viewer) can be ignored and a different prioritization for selection and placement of objects can be followed by the computing device executable instructions providing this functionality to the user.

Figure 3:
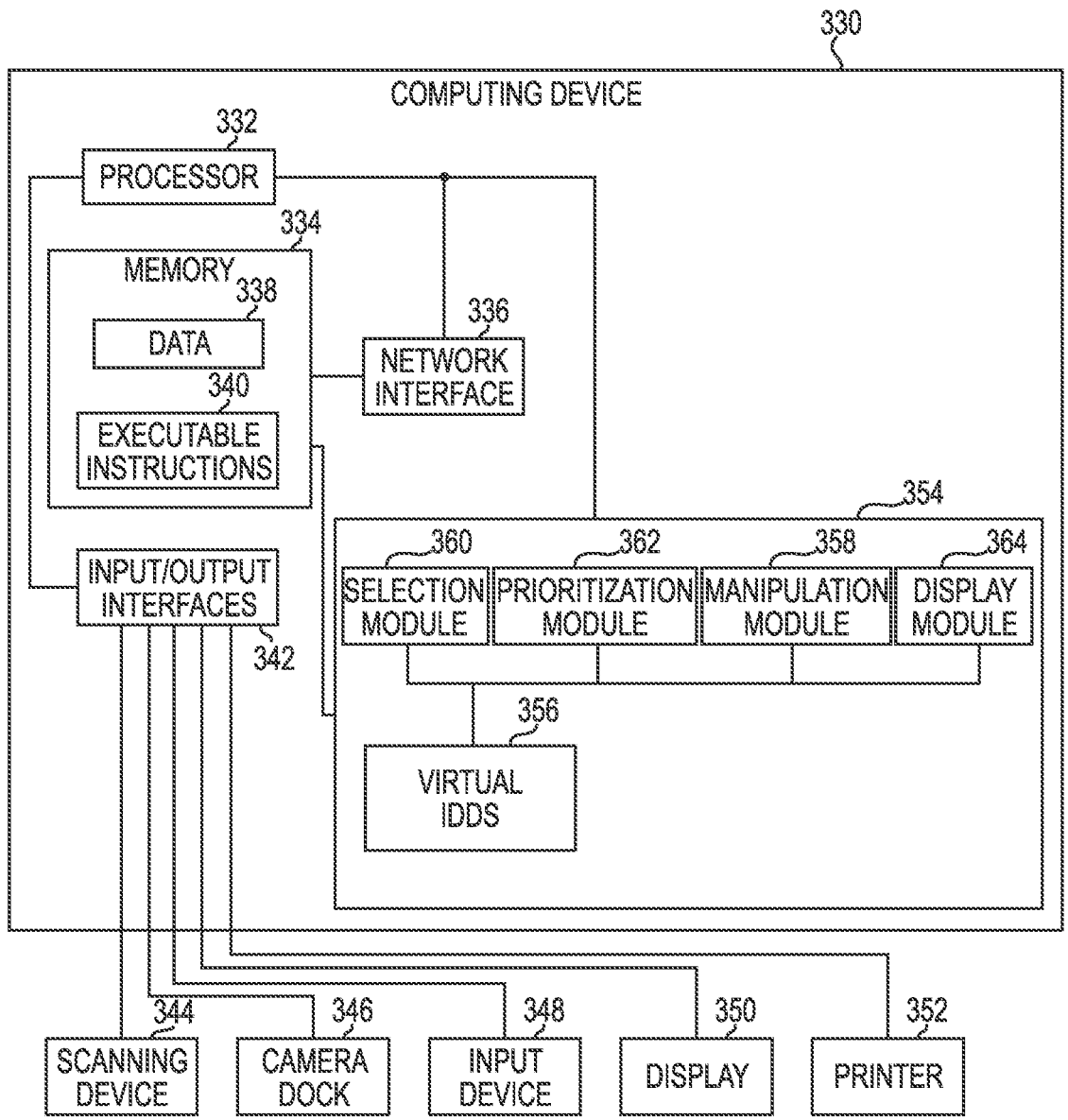
FIG. 3 illustrates a system for prioritizing 3D dental elements according to one or more embodiments of the present disclosure.

FIG. 3 illustrates a system for prioritizing 3D dental elements according to one or more embodiments of the present disclosure. In the system illustrated in FIG. 3, the system includes a computing device 330 having a number of components coupled thereto. The computing device 330 includes a processor 332 and memory 334. The memory can include various types of information including data 338 and executable instructions 340, as discussed herein.

Memory can be a non-transitory computing device readable medium that provides volatile or nonvolatile memory. The memory can also be removable (e.g., portable memory or non-removable, e.g., internal memory). For example, the memory can be random access memory (RAM) or read-only memory (ROM).

Memory can, for example, be dynamic random access memory (DRAM), electrically erasable programmable read-only memory (EEPROM), flash memory, phase change random access memory (PCRAM), compact-disk read-only memory (CD-ROM), a laser disk, a digital versatile disk (DVD) or other optical disk storage, and/or a magnetic medium such as magnetic cassettes, tapes, or disks, among other types of memory. Items stored in memory can include instructions executable by a computing device processor and/or data and the memory and processor can be located in one device or different devices.

Memory and/or the processor may be located on the computing device 330 or off the device, in some embodiments. As such, as illustrated in the embodiment of FIG. 3, a system can include a network interface 336. Such an interface can allow for processing on another networked computing device, can be used to obtain information about the patient, and/or can be used to obtain data and/or executable instructions for use with various embodiments provided herein.

As illustrated in the embodiment of FIG. 3, a system can include one or more input and/or output interfaces 342. Such interfaces can be used to connect the computing device with one or more input and/or output devices.

For example, in the embodiment illustrated in FIG. 3, the system can include connectivity to a scanning device 344, a camera dock 346, an input device 348 (e.g., a keyboard, mouse, etc.), a display device 350 (e.g., a monitor), a printer 352, and/or one or more other input devices. The input/output interface 342 can receive executable instructions and/or data, storable in the data storage device (e.g., memory 334), representing a digital dental model of a patient's dentition.

In some embodiments, the scanning device 344 can be configured to scan one or more physical molds of a patient's dentition. In one or more embodiments, the scanning device 344 can be configured to scan the patient's dentition directly. The scanning device 344 can be configured to input data into the computing device wherein the data can be provided to the application modules 354.

The camera dock 346 can receive an input from an imaging device (e.g., a two-dimensional or 3D imaging device) such as a digital camera, a printed photograph scanner, or other suitable imaging device. The input from the imaging device can, for example, be stored in the data storage device (e.g., memory 334).

The processor 332 can be configured to provide a visual indication of a virtual dental model on the display 350 (e.g., on a graphical user interface (GUI) running on the processor 332 and visible on the display 350). The GUI can be configured to allow a treatment professional or other user to input treatment goals, to create a virtual dental model, adjust priority levels, adjust references and other dental elements, and/or enter desired or actual attachment parameters. Input received via the GUI can be sent to the processor 332 as data and/or can be stored in memory 334.

Such connectivity can allow for the input and/or output of data and/or instructions among other types of information. Although some embodiments may be distributed among various computing devices within one or more networks, such systems as illustrated in FIG. 3, can be beneficial in allowing for the capture, calculation, and/or analysis of information discussed herein.

The processor 332, in association with the data storage device (e.g., memory 334), can be associated with data and/or application modules 354. The processor 332, in association with the memory 334, can store and/or utilize data and/or execute instructions to provide a number of application modules for prioritizing 3D dental elements. As used herein, a module can be a stand alone program, a portion of a program, or a set of code that provides a particular functionality.

Such data can include virtual IDDS 356. Such application modules can include a selection module 360, a prioritization module 362, a manipulation module 358, and/or a display module 364.

The selection module 360 can, for example, be configured to select a first element of a number of teeth in the virtual IDDS to be presented more transparently and a second element of the number of teeth in the virtual IDDS to be presented more opaquely.

The prioritization module 362 can be configured to prioritize the first and second elements based on the selection, and the manipulation module 358 can be configured to manipulate the first and second elements based on the prioritization, the transparency, and the opaqueness. In some embodiments, a user can determine a prioritization, and in other embodiments, the prioritization can be determined via computing device executable instructions. The display module 364 can be configured to display the manipulation on display device 350.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of appliances" can refer to one or more appliances.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A system for viewing three-dimensional (3D) dental elements, comprising:
 a memory having computer-readable instructions stored thereon; and
 a processor coupled to the memory to execute the computer-readable instructions to:
  receive a dental data set including spatial information regarding presentation of dental elements in a virtual 3D space to be viewed on a user interface, the dental elements including a first dental element and a second dental element;
  display the first dental element and the second dental element such that the first dental element is in front of at least a portion of the second dental element, wherein the first dental element is at least partially transparent such that the at least a portion of the second dental element is visible through the first dental element, wherein a first reference point is movable along a surface of the first dental element in preference over the second dental; and
  receive input from a user to move a second reference point, different from the first reference point, along a surface of the at least a portion of the second dental element without changing a transparency of the first dental element such that the second reference point is viewable through the first dental element.

2. The system of claim 1, wherein the first dental element and the second dental element are different teeth in a patient's dentition.

3. The system of claim 1, wherein the first dental element and the second dental element are different types of dental elements in a patient's dentition, the different types of dental elements including one or more of: gingiva, teeth and implants in the patient's dentition.

4. The system of claim 1, wherein the first dental element is a first tooth, and the second dental element is a second tooth, wherein the first reference point or the second reference point is a contact point of the first tooth and the second tooth.

5. The system of claim 1, wherein the first dental element is a first tooth, and the second dental element is a second tooth, wherein the first reference point is movable along an edge of the first tooth, and the second reference point is movable along an edge of the second tooth.

6. The system of claim 1, wherein the first dental element includes one or more teeth and the second dental element includes at least a portion of gingiva.

7. The system of claim 1, wherein the first reference point is adhered to the first dental element when the first reference point is movable along the surface of the first dental element, and wherein the second reference point is adhered to the second dental element when the second reference point is movable along the surface of the second dental element.

8. The system of claim 1, wherein the first reference point cannot be removed from the surface of the first dental element when the first reference point is movable along the surface of the first dental element, and the second reference point cannot be removed from the surface of the second dental element when the second reference point is movable along the surface of the second dental element.

9. The system of claim 1, wherein the computer readable instructions further comprise instructions to label one or more landmarks on the at least a portion of the second dental element behind the first dental element.

10. The system of claim 9, wherein the dental data set is a first dental data set, wherein the computer readable instructions further comprise instructions to transfer the one or more landmarks to a second dental data set that includes spatial information of the dental elements at a different time than the first dental data set.

11. The system of claim 1, wherein receiving the input from the user comprises receiving input from an input device, wherein the input device comprises a keyboard or a mouse.

12. A method of viewing three-dimensional (3D) dental elements, comprising:
   receiving a dental data set including spatial information regarding presentation of dental elements in a virtual 3D space to be viewed on a user interface, the dental elements including a first dental element and a second dental element;
   displaying the first dental element and the second dental element such that the first dental element is in front of at least a portion of the second dental element, wherein the first dental element is at least partially transparent such that the at least a portion of the second dental element is visible through the first dental element, wherein a first reference point is movable along a surface of the first dental element; and
   receiving input from a user to move a second reference point, different from the first reference point, along a surface of the at least a portion of the second dental element without changing a transparency of the first dental element such that the second reference point is viewable through the first dental element.

13. The method of claim 12, wherein the first dental element and the second dental element are different teeth in a patient's dentition.

14. The method of claim 12, wherein the first dental element and the second dental element are different types of dental elements in a patient's dentition, the different types of dental elements including one or more of: gingiva, teeth and implants in the patient's dentition.

15. The method of claim 12, wherein the first dental element is a first tooth, and the second dental element is a second tooth, wherein the first reference point is movable along an edge of the first tooth, and the second reference point is movable along an edge of the second tooth.

16. The method of claim 12, wherein the first dental element includes one or more teeth and the second dental element includes at least a portion of gingiva.

17. The method of claim 12, wherein the first reference point is adhered to the first dental element when the first reference point is movable along the surface of the first dental element, and wherein the second reference point is adhered to the second dental element when the second reference point is movable along the surface of the second dental element.

18. A system for viewing three-dimensional (3D) dental elements, comprising:
   a memory having computer-readable instructions stored thereon; and
   a processor coupled to the memory to execute the computer-readable instructions to:
      receive a dental data set including spatial information regarding presentation of dental elements in a virtual 3D space to be viewed on a user interface, the dental elements including a first dental element and a second dental element;
      display the first dental element and the second dental element such that the first dental element is in front of at least a portion of the second dental element, the first dental element rendered with a transparency that allows at least a portion of the second dental element to be visible through the first dental element, wherein a first reference point is adhered to and movable with respect to the first dental element; and
      receive input from a user to move a second reference point along a surface of the second dental element and adhered to the second dental element without changing the transparency of the first dental element such that the second reference point is viewable through the first dental element.

19. The system of claim 18, wherein the first dental element and the second dental element are different teeth in a dentition.

20. The system of claim 18, wherein the first dental element and the second dental element are different types of dental elements in a dentition, the different types of dental elements including one or more of: gingiva, teeth and implants in the dentition.

* * * * *